United States Patent
Lubitz et al.

(10) Patent No.: US 7,399,476 B2
(45) Date of Patent: Jul. 15, 2008

(54) NUCLEIC ACID FREE GHOST PREPARATIONS

(75) Inventors: Werner Lubitz, Vienna (AT); Wolfgang Haidinger, Vienna (AT)

(73) Assignee: Werner Lubitz, Klosterneuburg/Kritzendorf (AT)

( * ) Notice: Subject to any disclaimer, the term of this patent is extended or adjusted under 35 U.S.C. 154(b) by 60 days.

(21) Appl. No.: 10/483,595

(22) PCT Filed: Jul. 11, 2002

(86) PCT No.: PCT/EP02/07758

§ 371 (c)(1),
(2), (4) Date: Jan. 12, 2004

(87) PCT Pub. No.: WO03/006630

PCT Pub. Date: Jan. 23, 2003

(65) Prior Publication Data

US 2004/0213810 A1    Oct. 28, 2004

Related U.S. Application Data

(60) Provisional application No. 60/304,595, filed on Jul. 11, 2001.

(51) Int. Cl.
*A61K 39/02* (2006.01)
*A61K 38/00* (2006.01)
*C12P 21/06* (2006.01)

(52) U.S. Cl. ............... 424/200.1; 424/93.2; 424/234.1; 424/93.1; 514/2; 435/69.1; 435/320.1; 435/199; 536/23.1; 536/23.2; 536/23.7

(58) Field of Classification Search ........... 424/234.1, 424/184.1, 200.1, 93.1, 93.2, 93.4; 514/2; 435/69.1, 252.3, 320.1, 199, 235.1, 23.7; 536/23.1, 23.2, 23.7
See application file for complete search history.

(56) References Cited

U.S. PATENT DOCUMENTS 6,177,083 B1 * 1/2001 Lubitz ................. 424/234.1

FOREIGN PATENT DOCUMENTS

WO    WO-95/10614    * 4/1995

OTHER PUBLICATIONS

Haidinger et al., "Green Fluorescent protein (GFP)-dependent separation of bacterial . . . " Cytometry, vol. 44, No. 2, Jun. 1, 2001, pp. 106-112.
Szostak et al., "Bacterial ghosts as multifunctional vaccine particles", Behring Institute, No. 98, 1997, pp. 191-196.
Szostak et al., "Bacterial ghosts: non-living candidate vaccine", Journal of Biotechnology, Elsevier Science Publishers, vol. 44, No. 1, Jan. 26, 1996, pp. 161-170.
Lubitz et al., "Extended recombinant bacterial ghost system", Journal of Biotechnology, Elsevier Science Publishers, vol. 73, No. 2-3, Aug. 20, 1999, pp. 261-273.
Eko et al., "New strategies for combination vaccines based on the extended recombinant bacterial ghost system", Vaccine, Butterworth Scientific., vol. 17, No. 13-14, Jan. 1999, pp. 1643-1649.
Mader et al., "Endotoxicity does not limit the use of bacterial ghosts as candidate vaccines", Vaccine, Butterworth Scientific, vol. 15, No. 2, Feb. 1, 1997, pp. 195-202.
Huter et al., "Bacterial ghosts as drug carrier and targeting vehicles", Journal of Controlled Release, vol. 61, No. 1-2. Aug. 27, 1999, pp. 51-63.

* cited by examiner

*Primary Examiner*—Jon Weber
*Assistant Examiner*—Rita Mitra
(74) *Attorney, Agent, or Firm*—Rothwell, Figg, Ernst & Manbeck pc

(57) ABSTRACT

The invention relates to preparations of bacterial ghosts which are substantially free of living bacterial cells and/or nucleic acids and their use in pharmaceutical preparations.

15 Claims, 4 Drawing Sheets

SEQUENCE LISTING

```
<160> NUMBER OF SEQ ID NOS: 4

<210> SEQ ID NO 1
<211> LENGTH: 22
<212> TYPE: DNA
<213> ORGANISM: Escherichia coli
```

```
<400> SEQUENCE: 1
atgagccata ttcaacggga aa                                            22

<210> SEQ ID NO 2
<211> LENGTH: 23
<212> TYPE: DNA
<213> ORGANISM: Escherichia coli

<400> SEQUENCE: 2
ttagaaaaac tcatcgagca tca                                           23

<210> SEQ ID NO 3
<211> LENGTH: 24
<212> TYPE: DNA
<213> ORGANISM: Escherichia coli

<400> SEQUENCE: 3
atgagtattc aacatttccg tgtc                                          24

<210> SEQ ID NO 4
<211> LENGTH: 23
<212> TYPE: DNA
<213> ORGANISM: Escherichia coli

<400> SEQUENCE: 4
ttaccaatgc ttaatcagtg agg                                           23
```

NUCLEIC ACID FREE GHOST PREPARATIONS

CROSS REFERENCE TO RELATED APPLICATION

This application is a 35 USC §371 National Phase Entry Application from PCT/EP02/07758, filed Jul. 11, 2002, and designating the U.S., which claims priority of U.S. Provisional Application Ser. No. 60/304,595, filed Jul. 11, 2001. The disclosure of the International Application and the U.S. Provisional Application are hereby incorporated by reference.

The invention relates to preparations of bacterial ghosts which are substantially free of living bacterial cells and/or nucleic acids and their use in pharmaceutical preparations.

Empty bacterial membranes, so-called bacterial ghosts, are prepared by controlled heterologous expression of a gene which effects a partial lysis of the cellular membrane of bacteria, particularly gram-negative bacteria (EP-A-0 291 021). For example, the lytic gene may be the bacteriophage PhiX174 gene E encoding a polypeptide which is inserted into the cell membrane complex of gram-negative bacteria and leads to the formation of a transmembrane tunnel structure through the inner and outer membrane. The inner diameter of this tunnel structure is in the range of about 40 to 1,000 nm. The cytoplasmic components may be liberated by means of this tunnel structure, wherein an empty cell membrane having an intact morphology, a so-called bacterial ghost, is obtained. The use of bacterial ghosts as dead vaccines or adjuvants and the preparation of recombinant bacterial ghosts carrying heterologous surface proteins in their membrane structures is disclosed in WO91/13555 and WO93/01791.

Although the lytic process leading to an empty membrane without cytoplasmic structures is quite effective, a certain amount, usually about one cell in $10^4$ cells remains intact. In order to render even safer the use of bacterial ghosts as dead vaccines, particularly for applications in human medicine, it is necessary to provide ghost preparations, which contain a substantially lower number of living bacterial cells.

Surprisingly, it was found that the efficiency of the lytic process for the preparation of bacterial ghosts may be increased by co-expression of the lytic gene together with a gene encoding an enzyme which is present and hydrolytically active in the cytoplasm of the cell, wherein said enzyme is capable of hydrolyzing cytoplasmic compounds necessary for non-limited function of the cell, wherein the enzyme is preferably selected from nucleases, phospholipases, lipases, lysozymes, proteases and carbohydrases. The expression of such enzymes is described in EP-B-0 635 061. More preferably, the enzyme is a nuclease, particularly a truncated and/or mutated Staphylococcus aureus nuclease which is disclosed in WO95/10614.

Regulated co-expression of a bacterial lysis gene, e.g. the bacteriophage PhiX174 gene E and a nuclease gene, results in an synergistic increase of efficiency of the lytic process and correspondingly in a substantial reduction of living bacterial cells in a ghost preparation.

Thus, a first aspect of the present invention relates to a preparation of bacterial ghosts, which is substantially free of living bacterial cells. Preferably, the ratio of ghosts to living cells (determined as CFU by plating) is at least $10^6:1$, more preferably at least $10^7:1$, still more preferably at least $10^8:1$, and most preferably at least $10^9:1$.

Further, the present invention relates to a preparation of bacterial ghosts, which is substantially free of nucleic acids, particularly substantially free of nucleic acids having a length of $\geq 10$ nucleotides. Preferably, no nucleic acid is detected by Real Time-PCR having a lower detection limit of about 1-2 pg of DNA per $1 \times 10^6$, in particular per $2 \times 10^6$ ghosts and/or living or dead bacteria per ml. The Real Time-PCR is preferably carried out as described in Example 2 using suitable primers for a gene within the bacterial cell, e.g. an antibiotic resistance gene.

Further, the invention relates to a pharmaceutical composition comprising a preparation of bacterial ghosts as described above and a pharmaceutically acceptable carrier, diluent and/or adjuvant. The composition is suitable as a vaccine or an adjuvant, e.g. an immunostimulating compound, which is used together with an immunogen against which an immune-reaction shall be raised. The composition is suitable for use in human medicine and veterinary medicine. Moreover, the ghosts may be used as carriers for therapeutic and diagnostic agents.

Preferably, the ghosts are derived from gram-negative bacteria, which may be selected e.g. from Escherichia coli, Klebsiella, Salmonella, Pseudomonas, Vibrio, Actinobacillus, Haemophilus, Pasteurella, Bordetella and Helicobacter. Furthermore, the ghosts may be recombinant ghosts, i.e. ghosts carrying heterologous proteins, e.g. immunogens, in the membrane.

The ghosts may be administered according to known procedures, e.g. orally, intranasally, intraocularly, topically or parenterally. Depending on the mode of administration the composition may be formulated as an injectable or aerogenally applicable solution or suspension, as an oral composition, e.g. as tablet, capsule or dragée, as cream or ointment. Furthermore, the composition may be formulated as a reconstitutable lyophilisate.

The ghost preparation of the invention may be prepared by a method comprising the steps:

(a) providing bacterial cells comprising
  (i) a gene encoding a lytic protein capable of forming a tunnel structure in the bacterial membrane and
  (ii) a gene encoding an enzyme capable of hydrolyzing cytoplasmic components in the bacterial cells,
(b) optionally cultivating the bacterial cells under conditions, wherein the lytic gene and the enzyme gene are not expressed,
(c) subjecting the bacterial cells to conditions, wherein the lytic gene and the enzyme gene are expressed and the cytoplasmic components of the bacterial cells are degraded and liberated and
(d) obtaining the resulting bacterial ghosts.

Preferably, the lytic gene and the enzyme gene are in operative linkage with a regulatable expression control sequence. More preferably, the lytic gene and the enzyme gene are each in operative linkage with a separate, usually different regulatable expression control sequence.

Thus, the expression of both genes may be initiated separately, e.g. at different times of the cultivation procedure.

In a particularly preferred embodiment, the cells are cultivated under repressing conditions for both the lytic gene and the enzyme gene. Then, the expression of the enzyme is induced, e.g. when the enzyme gene is under control of a chemically regulatable promoter such as the lac promoter or a derivative thereof by adding an inducer, such as IPTG.

More preferably, the enzyme is expressed in a form which is at least partially inactive and which may be activated at a later stage by addition of a prosthetic group to the culture.

Then, subsequently, e.g. after 20 min up to 1.5 h, particularly preferably after about 45 min, the expression of the lytic gene is induced, e.g. when the lytic gene is in operative linkage with a temperature-regulatable promoter, such as the lambda PR or PL promoter by a temperature shift to 42° C. Then, after about 30 min up to 2 h, e.g. at about 90 min, the enzyme is activated by adding a prosthetic group required for its function, e.g. metal ions, such as $Mg^{2+}$ and/or $Ca^{2+}$.

Further, the invention relates to a bacterial cell comprising (i) a gene encoding a lytic protein capable of forming a tunnel structure in a bacterial membrane and (ii) a gene encoding an enzyme capable of hydrolyzing cytoplasmic components in the bacterial cell. This cell may be used as a starting material in a method for obtaining a preparation of bacterial ghosts, which is substantially free of living cells and/or which is substantially free of nucleic acids, particularly substantially free of nucleic acids having a length of $\geq 10$ nucleotides.

The lytic gene and/or the enzyme gene may be located on a vector, e.g. on the same vector or on different vectors. For example, the vector may be an extra-chromosomal plasmid having an origin of replication and a selection marker gene.

It should be noted that the disclosure of all patent documents recited in the specification above is incorporated herein by reference.

EXAMPLES

1. Preparation of Bacterial Ghosts using a Combination of E Lysis and Nuclease Treatment 1.1 Material The *E. coli* strain NM522 was used. The *E. coli* cells were transformed with the plasmid pML1, which is a lysis plasmid carrying the PhiX174 gene E under control of a wild type lambda promoter and a kanamycin resistance gene, or pSNUC1, which is a nuclease plasmid carrying the snuc gene (Genbank V01281, J01785, M10924; D. Shortle, Gene 22 (2-3), 181-189(1983)) under control of a lac promoter and an ampicillin resistance gene.

1.2 Experimental Design

The nuclease of the gram-positive bacterium *Staphylococcus aureus* is an enzyme which hydrolyzes nucleic acids due to its exonuclease and endonuclease activity. Experiments showed the combined expression of gene E and snuc increased the inactivation rate of ghosts and results in a reduced nucleic acid content.

1.3 Two-Vector Systems

In these systems protein E and SNUC are encoded on two different expression plasmids. Actually two different systems were tested.

| system | lysis plasmid | expr. of gene E | resistance | origin | SNUC plasmid | expr. of SNUC | resistance | origin |
|---|---|---|---|---|---|---|---|---|
| 1 | pML1 | cl857-pR | kanamycin | P15A | pSNUC1 | A1/O4/O3 | ampicillin | ColE1 |
| 2 | pAW12 | cl857-pR | tetracyclin | ColE1 | pHS SNUC | cl857-pR | kanamycin | P15A |

Best results were achieved using system 1 and following experimental design:

Overnight cultures of *E. coli* NM522 carrying plasmids pML1 and pSNUC1 grown at 28° C. with shaking were diluted in LB medium containing kanamycin and ampicillin to an $OD_{600}$ about 0.05 to 0.08. Cultures were grown at 28° C. with shaking to an $OD_{600}$ about 0.25 to 0.3 (time-45). Then IPTG was added in a final concentration of 5 mM to induce expression of SNUC. 45 minutes later the cultures were shifted to 42° C. (time 0) to induce expression of gene E. 90 minutes after shift (time 90) calcium ions and magnesium ions were added in final concentrations of 10 mM and 1 mM, respectively, to activate the enzymatic activity of SNUC.

$OD_{600}$ was measured at time-45 and after that in intervals of 30 minutes starting at time 0 and CFU (colony forming units) were determined at the following times: −45, 0, 30, 60, 90, 120, 180, 240, 300, 360, 420, 480, 540, 600 and 1320. These experiments resulted in total inactivation of *E. coli* within 6 to 22 hours.

2. Measurement of DNA Content in Bacterial Ghosts by Real Time-PCR

The residual DNA content was analyzed in the pellet as well as in the supernatant by agarose gel. In order to quantify the DNA content the concentration of kanamycin resistance gene and ampicillin resistance gene corresponding to the number of plasmids pSNUC1 and pML1, respectively, was measured by Real Time-PCR.

2.1 Devices and Chemicals

Real Time Cycler: Corbett Research (distribution: genXpress Service & Vertrieb GmbH, Vienna, Austria)
Polymerase: Dynazyme (Finzyme)
DNA-dye: SYBR-Green I 10,000×(Molecular Probes)
dNTPs: 10 mM each (Roche)

| Components | Amount in µl for 1 batch (25 µl) | Amount in µl for 20 batches (500 µl) |
|---|---|---|
| Polymerase buffer | 2.5 | 50 |
| Polymerase | 0.25 | 5 |
| Primer 1 | 0.1 | 2 |
| Primer 2 | 0.1 | 2 |
| dNTPs (10 mM each) | 0.5 | 10 |
| SYBR 1 (10× in $H_2O$) | 0.25 | 5 |
| $H_2O$ | 20.8 | 416 |
| Template-DNA | 0.5 | (10) |

| | | |
|---|---|---|
| | 94° C. | 2 min |
| 40 cycles: | 94° C. | 28 sec |
| | 60° C. for Kan (62° C. for Amp) | 1 min |
| | 72° C. | 1 min |
| | 4° C. | until the end |
| fusion curve: | 50° C.-96° C. | |

```
Primer:

[SEQ ID NO: 1]
Kan-start:  5'-atgagccatattcaacgggaaa-3'

[SEQ ID NO: 2]
Kan-stop:   5'-ttagaaaaactcatcgagcatca-3'

[SEQ ID NO: 3]
Amp-start:  5'-atgagtattcaacatttccgtgtc-3'

[SEQ ID NO: 4]
Amp-stop:   5'-ttaccaatgcttaatcagtgagg-3'
```

2.4 DNA-Templates

Plasmid Standards

The plasmids pSNUC1 and pML1 were prepared from overnight cultures (28° C./Amp or rather Kan) of *E. coli* NM522 via alkaline lysis and stored at 4° C. after RNase-treatment in TE-buffer. The absolute DNA amounts of the plasmid standards were determined fluorimetrically: the standards were prepared from calf-thymus-DNA and after dyeing with the DNA-dye HOECHST 33342 (molecular probes) a calibrating plot was prepared. The plasmid standards were also treated with the dye and analyzed fluorometrically. From the calibration straight line the DNA-content in the plasmid samples could be determined.

pML1: 0.32 µg/µl
pSNUC1: 0.19 µg/µl

From these master-plasmid-standards the dilutions (up to $10^{-7}$) were produced in a TE-buffer.

| Standard dilution | pSNUC1-concentration/µl | pML1-concentration/µl |
|---|---|---|
| original | 190 ng | 320 ng |
| $10^{-1}$ | 19 ng | 32 ng |
| $10^{-2}$ | 1.9 ng | 3.2 ng |
| $10^{-3}$ | 190 pg | 320 pg |
| $10^{-4}$ | 19 pg | 32 pg |
| $10^{-5}$ | 1.9 pg | 3.2 pg |
| $10^{-6}$ | 190 fg | 320 fg |
| $10^{-7}$ | 19 fg | 32 fg |

Samples from Lysed Cultures

Every time 1 ml culture was taken and centrifuged. 0.5 ml of the supernatant were analyzed, the remainder thrown away.

The pellet (from 1 ml culture) was subjected to a total DNA preparation (Easy-DNA; invitrogen) and the preparation added to 100 µl TE+RNase.

The supernatant (from 0.5 ml culture) was two times extracted with phenol/chloroform and precipitated with ethanol. The pellet was added to 50 µl TE+RNase.

In order to quantify the samples from lysed cultures the plasmid standards $10^{-2}$, $10^{-4}$ and $10^{-5}$, a zero control (without DNA template) and a number (10-12) of DNA samples were analyzed simultaneously. All of the samples (including zero-control and standards) were analyzed in a double batch via real time-PCR.

Each time 0.5 µl of the DNA-preparations were employed as templates.

After concentration values with regard to the genes to be quantified had been assigned to the plasmid standards, the quantification of the samples was performed completely automatically by the PCR-apparatus. DNA-samples, which led to an increase in the product yield in the real-time kinetics only after the standard $10^{-5}$, or provided no signal or one too weak, similar to the standards $10^{-6}/10^{-7}$, were regarded as being "below the detection limit" when determining the concentration.

2.5 Real Time-PCR

The plasmid standards produced (dilutions $10^{-1}$-$10^{-7}$) were analyzed by means of real time-PCR, in order to determine the detection limits. After analysis of the data of the Real Time-PCR-measurements and the fusion curves those dilutions of further analyses were excluded, which provided no signal or a signal too weak. Those fluorescence values were considered to be signals too "weak", which were derived from PCR-product-amounts that turned out to be smaller than the average plateau value of the higher standards, whereby the "correct" product (Kan/Amp) provided the smaller portion of the fluorescence signal.

At both standard curves a linear measurement range within the concentration range of $10^{-1}$-$10^{-5}$ could be found.

Detection limits: pML1: 1.67 pg (0.5 µl in dilution $10^{-5}$)
pSNUC1: 1 pg (0.5 µl in dilution $10^{-5}$)

3. FIGURES

Figure 1:
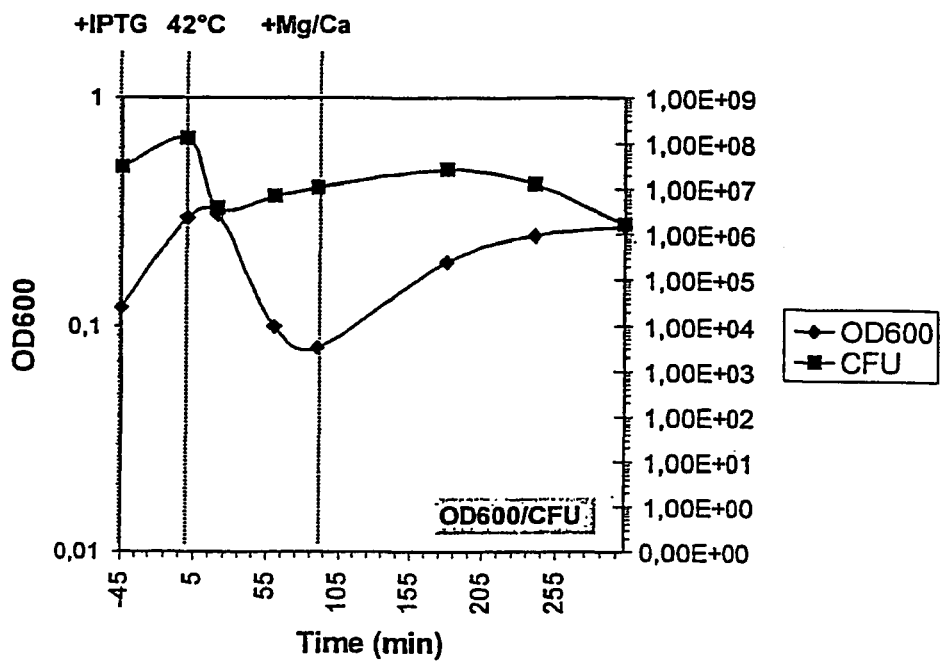
FIG. 1 shows the lysis kinetics after expression of the lysis gene E in *E. coli* NM522 (pML1).
Figure 2:
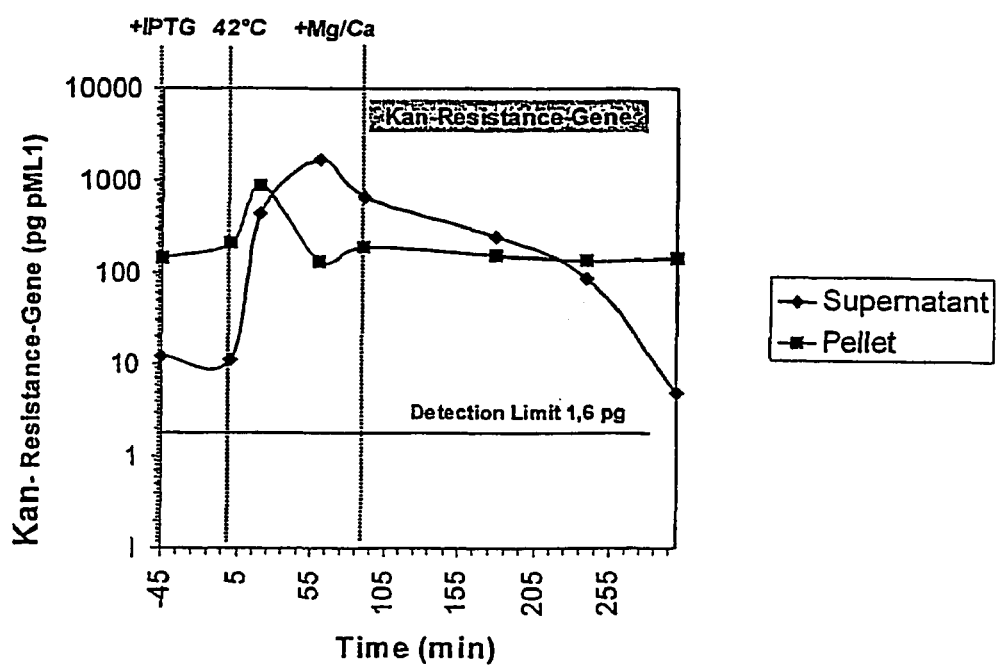
FIG. 2 shows the results of a real-time PCR (kanamycin resistance gene) in *E. coli* NM522 (pML1) cells.
Figure 3:
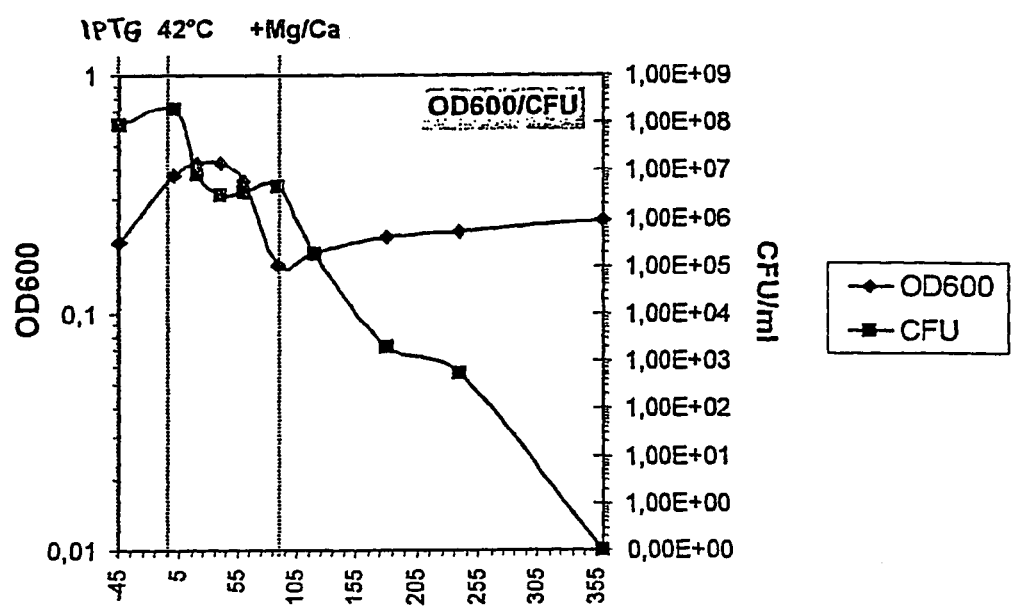
FIG. 3 shows the lysis kinetics after co-expression of lysis gene E and staphylococcal nuclease (SNUC) in *E. coli* NM522 (pML1+pSNUC).
Figure 4A:
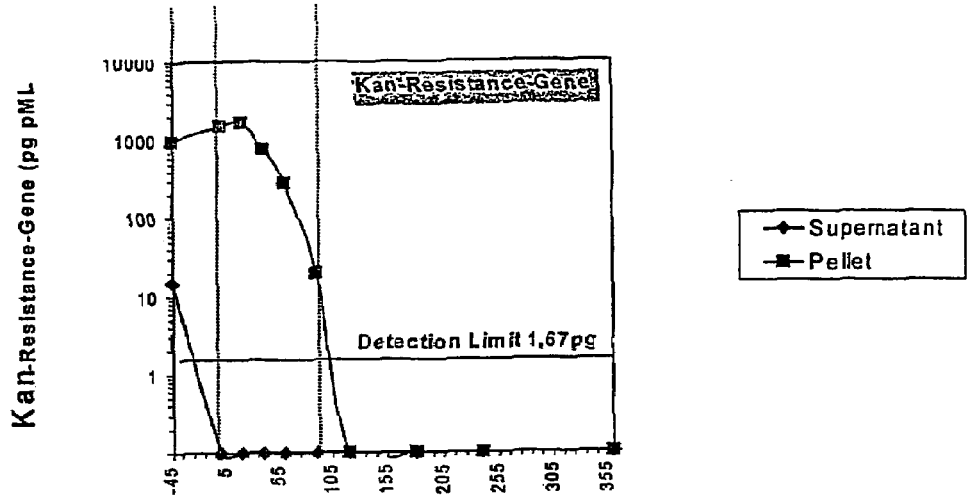
FIGS. 4a and 4b show the results of a real-time PCR (kanamycin and ampicillin resistance gene) in *E. coli* NM522 (pML1+pSNUC).
Figure 4B:
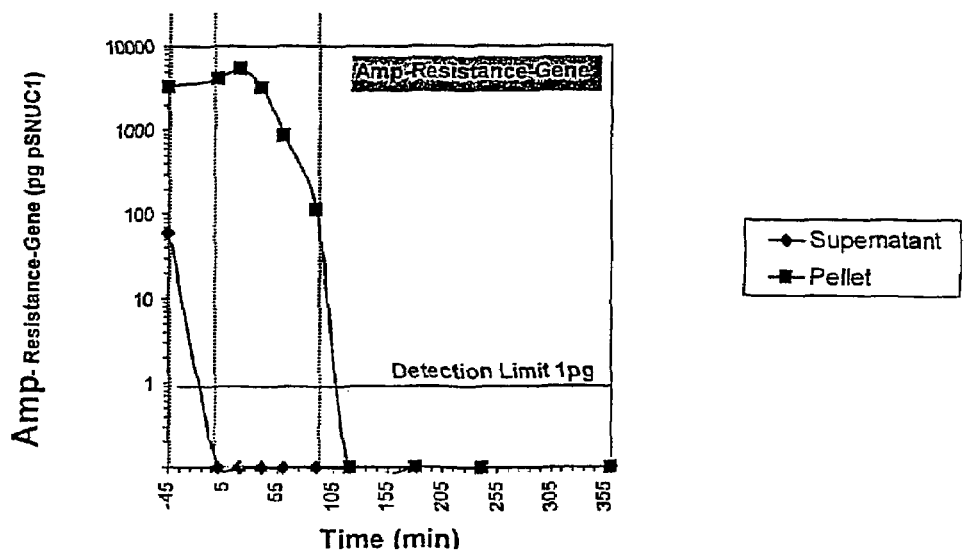

From a comparison between FIGS. 1 and 2 (prior art) and the FIGS. 3 and 4 (present invention) it can be seen that by the co-expression of lytic gene and nuclease gene a surprising reduction of the living bacterial cells (expressed as CFU) and the nucleic acids (expressed as result of the real-time PCR) is obtained.

From this comparison the advantages achieved by the present invention can be clearly gathered.

The invention claimed is:

1. A preparation of bacterial ghosts which is substantially free of living bacterial cells, wherein the ratio of ghosts to living cells is at least $10^6$:1.

2. The preparation of claim 1, wherein the ratio of ghosts to living cells is at least $10^8$:1.

3. A pharmaceutical composition comprising the preparation of claim 1 and a pharmaceutically acceptable carrier, diluent and/or adjuvant.

4. The composition of claim 3 which is a vaccine.

5. The composition of claim 3 which is an adjuvant.

6. The composition of claim 3 for use in human medicine.

7. The composition of claim 3 for use in veterinary medicine.

8. A method for obtaining a preparation of bacterial ghosts of claim 1 comprising the steps:
   (a) providing bacterial cells comprising
      (i) a gene encoding a lytic protein capable of forming a tunnel structure in the bacterial membranes and
      (ii) a gene encoding an enzyme capable of hydrolyzing cytoplasmic components in the bacterial cells, wherein said enzyme is a nuclease,
   (b) optionally cultivating the bacterial cells under conditions wherein the lytic gene and the enzyme gene are not expressed,
   (c) subjecting the bacterial cells to conditions wherein the lytic gene and the enzyme gene are expressed and the cytoplasmic components of the bacterial cells are degraded and liberated and
   (d) obtaining the resulting bacterial ghosts.

9. The method of claim 8, wherein the gene encoding the lytic protein is the bacteriophage phiX174 gene E.

10. The method of claim 8, wherein the nuclease is a *Staphylococcus aureus* nuclease.

11. The method of claim 8, wherein the lytic gene and the enzyme gene are in operative linkage with a regulatable expression control sequence.

12. The method of claim 11, wherein the lytic gene and the enzyme gene are each in operative linkage with a separate regulatable expression control sequence.

13. The method of claim 12, wherein the expression of the lytic gene and the expression of the enzyme are induced at different times.

14. A preparation of bacterial ghosts which is substantially free of nucleic acids.

15. An isolated bacterial cell comprising
   (i) a gene encoding a lytic protein capable of forming a tunnel structure in the bacterial membrane and
   (ii) a gene encoding an enzyme capable of hydrolyzing cytoplasmic components in the bacterial cell,
   wherein said lytic gene and/or enzyme gene are located on one or several plasmid vectors.

* * * * *